United States Patent [19]

Apperson et al.

[11] Patent Number: 5,106,374
[45] Date of Patent: Apr. 21, 1992

[54] AMBULATORY INFUSION DEVICE

[75] Inventors: Curtis R. Apperson, Green Oaks; Urban M. Ebert, Lake Bluff; Alice Chang, Westmont; Robert A. Weisenbach, Libertyville, all of Ill.

[73] Assignee: Abbott Laboratories, Abbott Park, Ill.

[21] Appl. No.: 521,791

[22] Filed: May 8, 1990

[51] Int. Cl.⁵ .................................. A61M 37/00
[52] U.S. Cl. ........................... 604/140; 604/141; 604/131; 128/DIG. 12
[58] Field of Search ............... 604/140, 141, 142, 148, 604/132, 153, 143, 146, 147, 131; 128/DIG. 12, 13; 417/395

[56] References Cited

U.S. PATENT DOCUMENTS

| | | | |
|---|---|---|---|
| 3,640,277 | 2/1972 | Adelberg | 604/141 |
| 3,895,741 | 7/1975 | Nugent | 604/141 |
| 4,168,288 | 9/1979 | Nav et al. | 417/395 |
| 4,237,881 | 12/1980 | Beigler et al. | 604/141 |
| 4,539,005 | 9/1985 | Greenblatt | 604/141 |
| 4,784,652 | 11/1988 | Wikstrom | 604/148 |

Primary Examiner—Gene Mancene
Assistant Examiner—Michael Lynch
Attorney, Agent, or Firm—A. Nicholas Trausch

[57] ABSTRACT

The present invention is directed to an ambulatory infusion device having a housing which has a series of cavities in which there are provided expandable pressure regulator tubes which may be formed of suitable resilient materials. The regulator tubes may be of several different configurations. The cavities have a greater volume than the expandable tubes to permit expansion thereof and also to provide means for limiting the expansion thereof to ensure against bursting of the tubes should a pressure relief valve in the system fail to operate. The open ends of the regulator tubes are interconnected through a series of passageways, connectors, etc. to an inflatable, flexible, substantially non-stretchable diaphragm provided in another housing cavity. A fresh flexible bag of medicament is positioned against the diaphragm by the patient with an administration port of the bag projecting outwardly of the housing for connection to an infusion set connectable to a patient's catheter. The pressure source for this system is a container of pressurized gas, such as nitrogen, which is insertable into another cavity for interconnection with the regulator tubes through the passageways. When the gas is released from the pressurized cannister, the system becomes charged with the regulator tubes being expanded a desired amount. The infusion process is then initiated by release of a clamp on the patient's infusion set whereupon the regulator tubes gradually deflate due to the resiliency thereof with the substantially non-expandable diaphragm being inflated against the flexible medicament bag. The medicament is infused at a substantially steady rate into the patient until the medicament bag has been emptied.

14 Claims, 7 Drawing Sheets

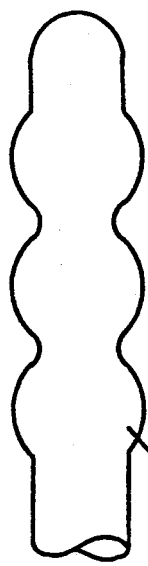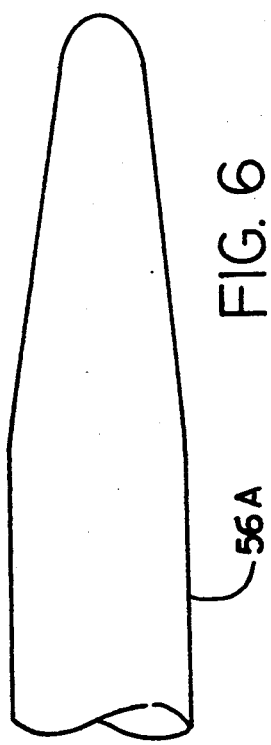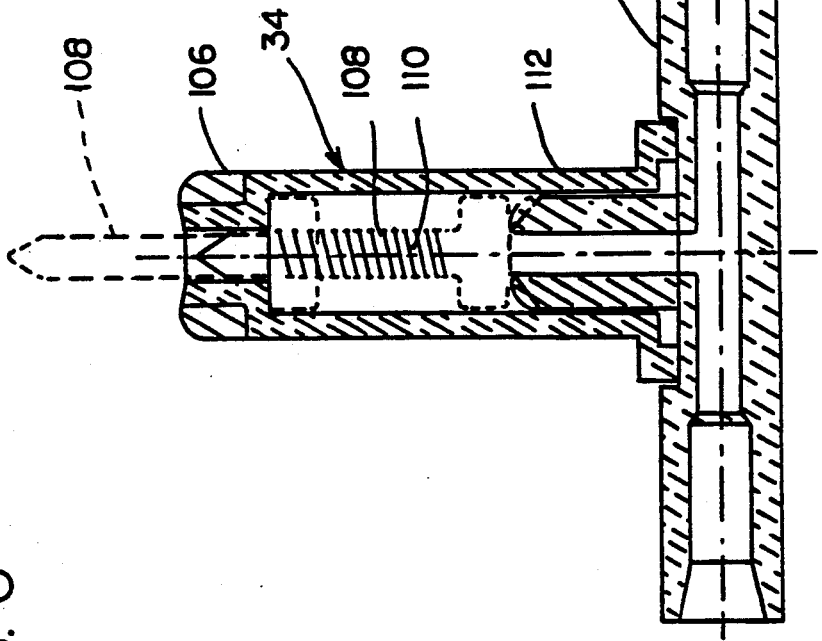

AMBULATORY INFUSION DEVICE

BACKGROUND OF THE INVENTION

In situations where a patient requires intermittent infusion or continuous slow introduction of a medicament, such as an antibiotic, into his or her system, the usual delivery modes involve gravity flow or a flow control infusion pump. These delivery modes have limitations for patients that can be ambulatory. For gravity flow, the patient is incapacitated or tied down to an IV pole from which the bag or bags of medicament are hung during the entire infusion process which may last a matter of hours. Known infusion pumps tend to be heavy, expensive and require a power source. In a nutshell, all of the aforesaid delivery modes are very limiting in lifestyle for the patient.

Ambulatory infusion devices which have been tried include various types of pneumatic, spring powered or portable electronic pump devices. Inasmuch as a goodly number of patients requiring such medicament infusion are either aged, in a weakened condition, or, conversely, desirous of being highly mobile, such attempts have not been successful due to the bulk, weight, cost and the reliability of such devices.

Previous ambulatory attempts are disclosed for example in U.S. Pat. No. 3,640,277, which includes a pneumatic system having a complex mechanical valving system. U.S. Pat. No. 3,153,414 requires constant monitoring of the bulb-pumped pressure. U.S. Pat. No. 4,507,116 is a pneumatic system which includes an elastic accumulator and diaphragm which reduces driving fluid pressure resulting in inconsistent flow rate.

SUMMARY OF THE INVENTION

The present invention is directed to an improved ambulatory infusion device which is relatively lightweight as it incorporates no pump or other mechanical apparatus. It is small enough to be comfortably carried on the body in an out of the way location so that it does not hinder normal mobility of the patient during an infusion cycle which normally lasts an hour or more.

A substantial portion of the device is disposable after each infusion treatment and the entire unit is disposable after a day's worth of treatments.

Replacement kits are provided so that a patient may very easily replace the disposable elements between infusion sessions.

The device is characterized by a light-weight housing which has a series of cavities in which there are provided expandable pressure regulator tubes which may be formed of suitable resilient materials. As will be evident hereinafter, these regulator tubes may be of several different configurations. The cavities have a greater volume than the expandable tubes to permit expansion thereof and also to provide means for limiting the expansion thereof to ensure against bursting of the tubes should a pressure relief valve in the system fail to operate. The open ends of the regulator tubes are interconnected through a series of passageways, connectors, etc. to an inflatable, flexible, substantially non stretchable diaphragm provided in another housing cavity and adapted to have a fresh flexible bag of medicament positioned thereagainst by the patient with an administration port of the bag projecting outwardly of the housing for connection to an infusion set connectable to a patient's catheter. The pressure source for this system is a container of pressurized gas, such as nitrogen, which is insertable into another cavity for interconnection with the regulator tubes through the passageways. When the gas is released from the pressurized cannister, the system becomes charged with the regulator tubes being expanded a desired amount.

The infusion process is then initiated by release of a clamp on the patient's infusion set whereupon the regulator tubes gradually deflate due to the resiliency thereof with the substantially non-expandable diaphragm being inflated against the flexible medicament bag whereby the medicament is infused at a substantially steady rate into the patient until the medicament bag has been emptied.

The present invention is directed to a new and improved ambulatory infusion device which is lightweight and which incorporates disposable pneumatic components.

An object of the present invention is to provide a new and improved ambulatory infusion device wherein the pressure for the infusion process is provided by a lightweight pneumatic system including a container of pressurized gas, a series of expandable regulator tubes, and an inflatable, substantially non-stretchable diaphragm which is disposed against a flexible bag of medicament within a volume limiting cavity.

Another object of the present invention is to provide such a device wherein means are provided for clamping off a portion of the bag of medicament when same is of the type having an additive container associate therewith.

BRIEF DESCRIPTION OF THE DRAWINGS

FIG. 6 is a side elevation view of a tapered form of expandable regulator tube usable in the pressure system of FIG. 5;

FIG. 7 is a side elevation view of a pre-bulged form of expandable regulator tube usable in the pressure system of FIG. 5;

FIG. 12 is a sectional view taken through the pressure indicator of the infusion tube set of FIG. 2.

DESCRIPTION OF THE PREFERRED EMBODIMENT

Figure 1:
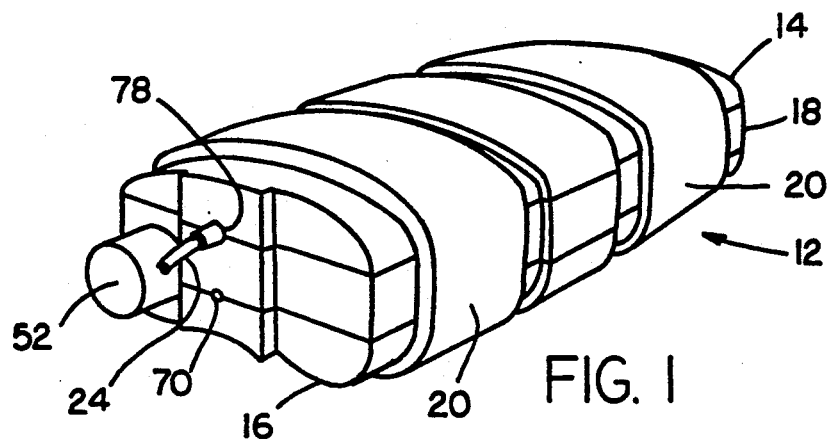
FIG. 1 is a perspective view of an assembled three-part housing embodying a preferred embodiment of the invention.
Figure 3:
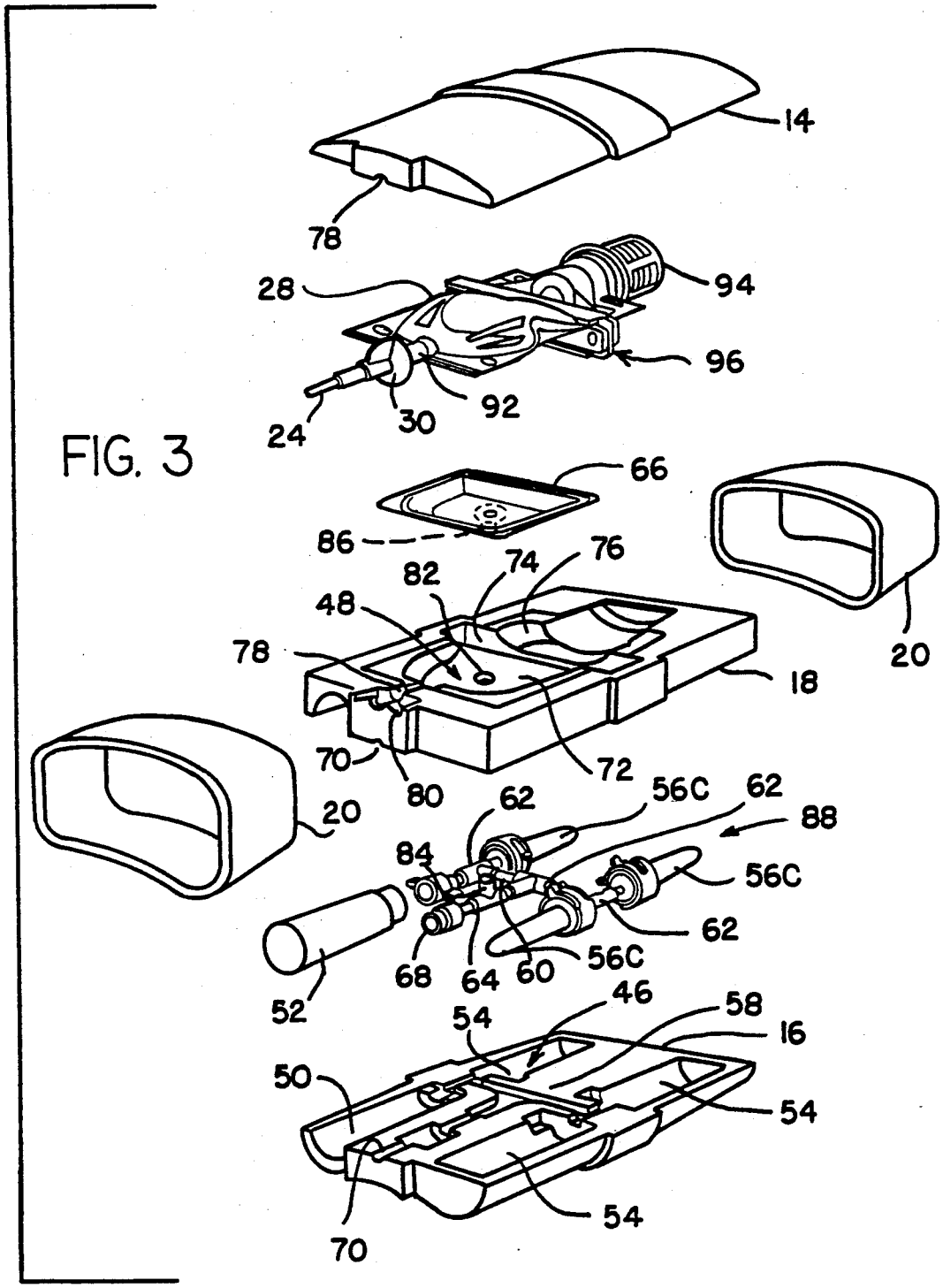
FIG. 3 is an exploded, perspective view of the embodiment of the invention shown in FIG. 1.

Referring now to the drawings, a preferred embodiment of the invention includes a three-part sandwich like housing 12 formed of a relatively strong but lightweight material such as modified expandable polystyrene foam. As best illustrated in FIG. 3, the housing 12 is characterized by an upper housing member 14, a lower housing member 16, and a middle housing member 18 which is sandwiched therebetween, all three members being generally rectangular in configuration. When assembled, the housing 12 tapers slightly from its mid-section toward its opposite ends so that rigid retaining slide rings 20 may be fitted over the opposite ends thereof, as best illustrated in FIG. 1, whereby to retain the three-part housing 12 in assembled relationship.

Figure 2:
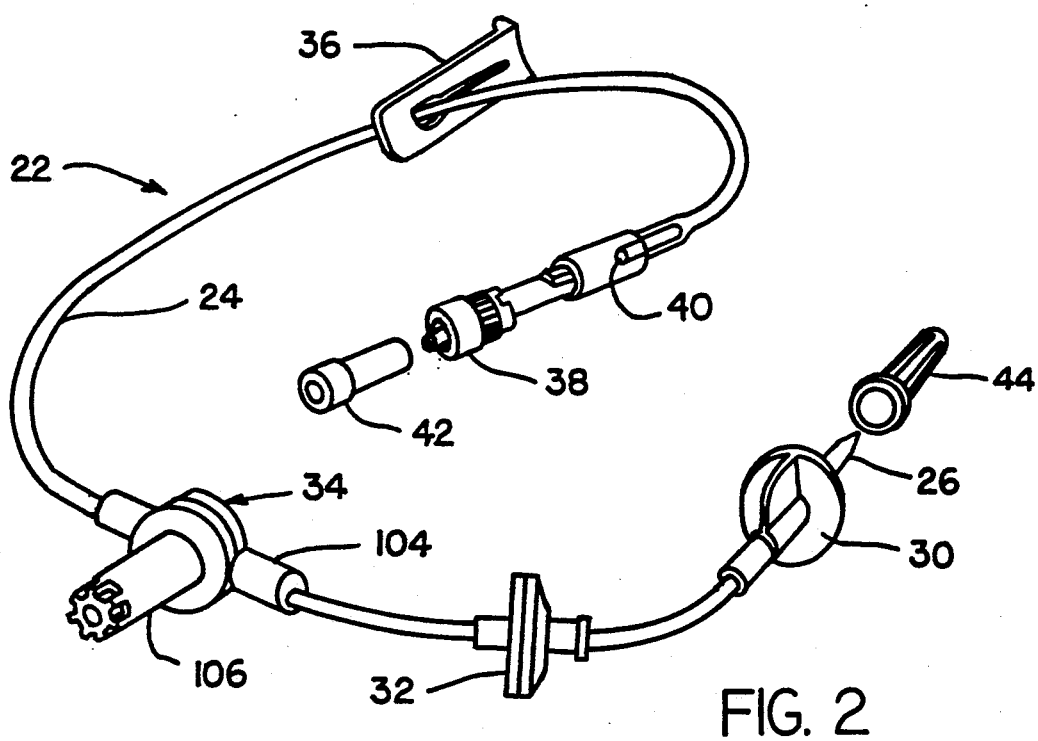
FIG. 2 is a perspective view of an infusion tube set usable with the embodiment of the invention shown in FIG. 1.
Figure 11:
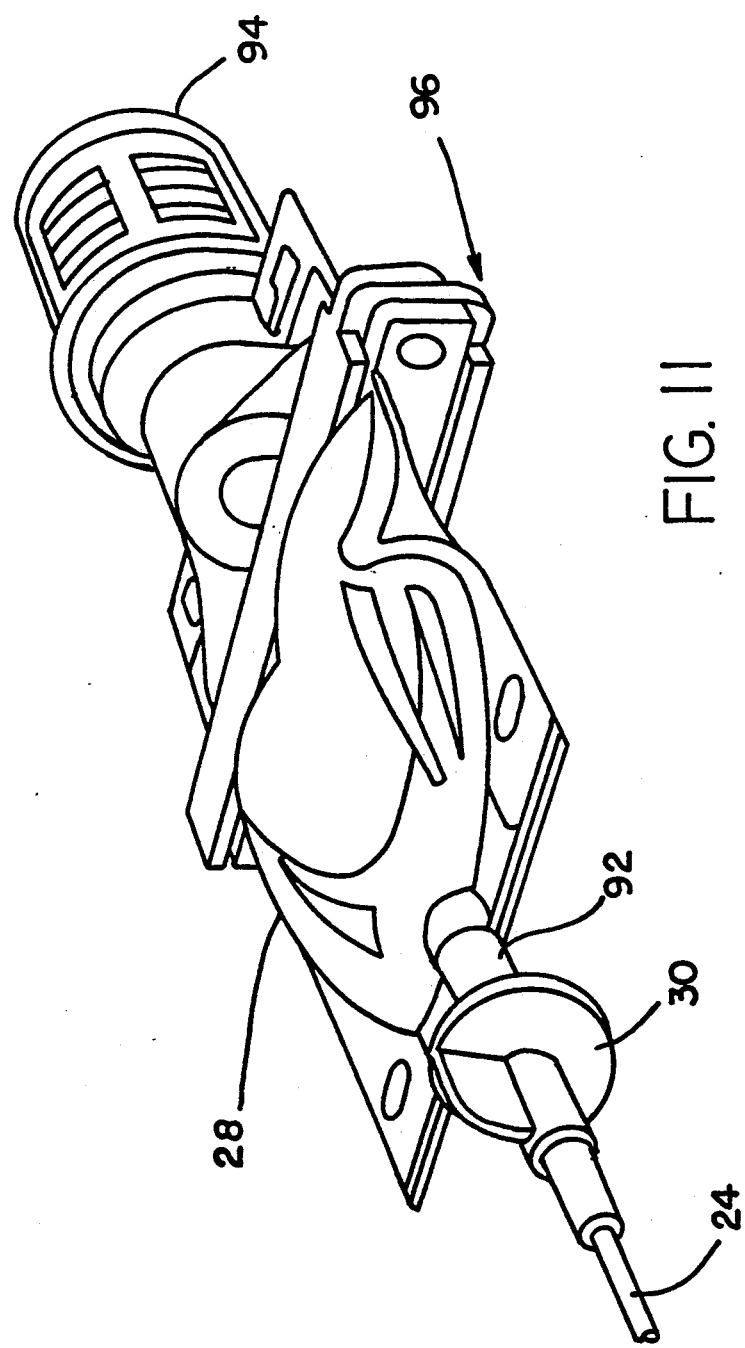
FIG. 11 is an enlarged perspective view of the medicament bag of FIG. 3 with an additive container associated therewith clamped off by a three-piece clamping device.

Before discussing the infusion pressure system provided in the housing 12, an infusion set 22 adapted for use with the new and improved ambulatory infusion device of the present invention will first be briefly described. As illustrated in FIG. 2, the infusion set 22 is characterized by I.V. tubing 24, a piercing pin 26 provided at one end and adapted for connection to a bag 28 of medicament positioned in the housing 12 (FIG. 11), a locating flange 30 adjacent the piercing pin 26, an air filter 32 of a type well-known in the art, a pressure indicator 34, a slide clamp 36 of a well-known type, and a luer connector 38 connectable to the proximal fitting 42 of a patient's catheter. A flow restrictor 40 having a pressure controlling orifice is positioned immediately prior to the connector 38. The length and diameter of the orifice 40 determines the pressure drop so a tube set 22 having the desired combination of orifice length and diameter may be selected for the proper flow rate of the drug to be administered with the ambulatory infusion device of the present invention. A protective sheath 44 may be provided for the piercing pin 26 until its connection to the medicament bag 28.

Figure 4:
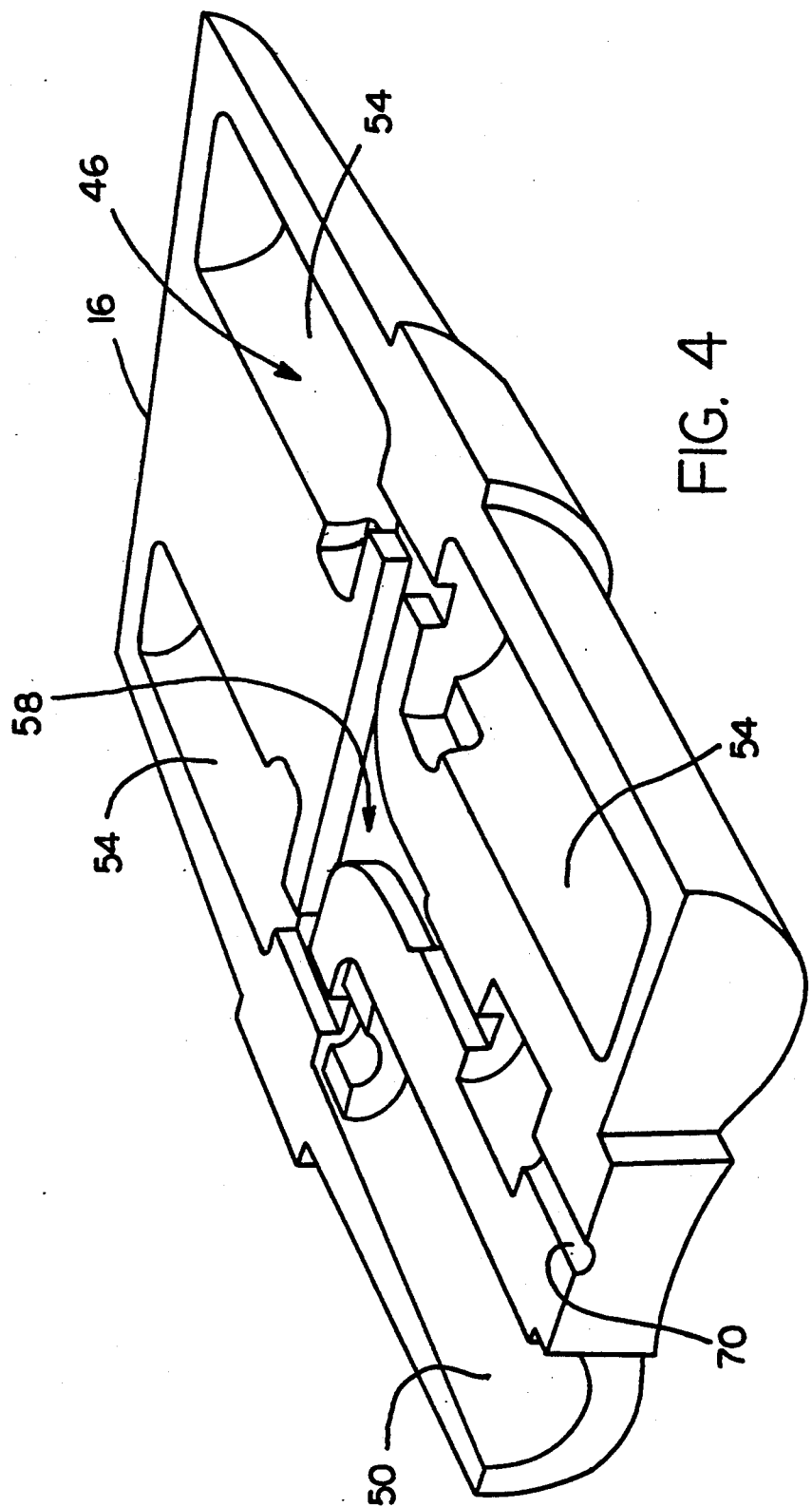
FIG. 4 is an enlarged perspective view of the lower housing member shown in FIG. 3.
Figure 5:
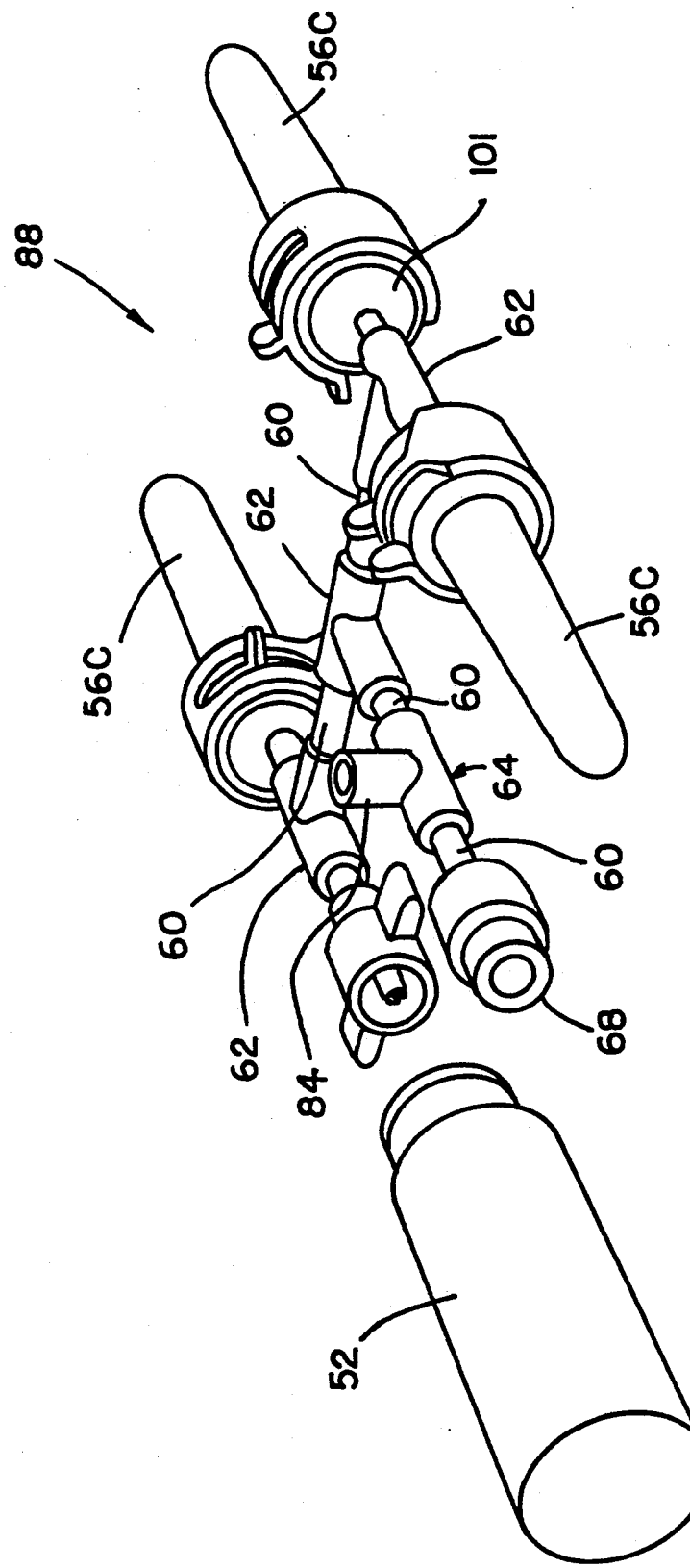
FIG. 5 is an enlarged perspective view of the infusion pressure system which is received in the cavities provided in the lower housing member shown in FIG. 4.

As best illustrated in FIG. 3, first mating cavity means 46 are provided in the upper surface of the lower housing member 16 and the underside of the middle housing member 18 and second mating cavity means 48 are provided in the upper surface of the middle housing member 18 and the underside of the upper housing member 14. Referring to FIGS. 4 and 5, the first cavity means 46 includes a generally cylindrical cavity 50 which is open at one end and which is adapted to have a pressurized container 52 of gas such as a cylinder of nitrogen at 65 psi, inserted therein by the device user. The container is activated by well-known means such as a threaded attachment fitting.

The cavity means 46 also includes at least two (three in the embodiment shown) cavities 54, each of which is adapted to receive therein an expandable pressure regulator tube 56 which may be formed of a suitable rubber-like material such as latex rubber or chlorinated natural rubber and which may be formed with any of several configurations, as illustrated in FIGS. 5, 6, 7, 8, 9 and 10. The volume of the cavities 54 must be larger than the desired final volume of the expanded regulator tubes 56. This permits the regulator tubes 56 to expand to the extent permitted by the expandability of the tubes 56 but provides a limit to such expansion to limit overexpansion should available pressure relief means fail.

The cavity means 46 contains a pressurized system 88 which includes a series of passageways 58 adapted to receive lengths of fluid tubing 60 and a series of T-connectors 62 for interconnecting a container 52 of pressurized gas inserted into the cavity 50 by the user with the expandable pressure regulator tubes 56 disposed in the cavities 54. The pressurized system 88 also includes a connector 64 to communicate fluid to the inflatable, flexible diaphragm 66, located in cavity 48. Also an over pressure relief valve 68 is provided with a relief passageway 70 to the atmosphere.

The second mating cavity means 48, which are provided between the upper surface of the middle housing member 18 and the underside of the upper housing member 14, includes a first pressure diaphragm cavity 72, a transversely disposed generally rectangular clamp cavity 74, and a second non-pressure cavity 76. The first bag cavity 72 is characterized by an outlet port 78 having a flange slot 80 associated therewith and, approximately at the center thereof, a bored opening 82 which extends through the middle housing member 18 to cavity 46 for receiving a vertically disposed portion 84 of the diaphragm connector 64. The inflatable, flexible substantially non-stretchable cavity shaped diaphragm 66 is fitted in the first bag cavity 72 and is connected to the vertically disposed portion 84 of the diaphragm connector 64 by a fitting 86 to complete the pressurizable system 88 of the ambulatory infusion device of the invention.

Whereas the middle 18 and lower 16 housing members are sealed together by a suitable adhesive after assembly of the regulator tubes 56, the diaphragm connector, 64, the pressure relief valve 68, the lengths of tubing 60 and the T-connectors 62 into the tube cavities 54 and the passageways 58, the upper housing member 14 is detachable after removal of the slip-rings 20 to permit the user to insert a bag 28 of medicament such as an antibiotic. This bag 28 will have an administration port 92 which will be received in the housing outlet port 78 after the bag is opened by the piercing pin 26. The piercing pin 26 on the infusion set 22 and the flange 30 are received in the flange slot 80.

In the embodiment illustrated in the drawings, the medicament bag 28 is of the type having an additive container 94 associated therewith, as is disclosed in U.S. Pat. No. 4,614,515. It is therefore necessary to clamp off the upper portion of the bag 28 carrying the now-emptied additive container 94 and a new and novel three-member clamp 96 is provided in the clamp cavity 74. This new and novel clamp 96 is fully disclosed in U.S. Pat. No. 4,996,267, titled CLAMP FOR FLEXIBLE BAG being filed concurrently herewith. With this arrangement, the sealed-off upper portion of the bag 28 is received in the second bag cavity 76.

After the patient has placed the medicament bag 28 in the cavities 72 and 76 and the clamp 96 has been closed, the upper housing member 14 is assembled and the slip-rings 20 are slipped over the opposite ends of the housing 12. The user then inserts the pressurized container 52 of pressurized gas in the cavity 50 after having made sure that the infusion tube set 22 has been closed by the clamp 36. When the pressurized gas container has been activated by the user, the pressure system 88 will be charged and ready for an infusion cycle. The passageways 58 and any dead space in the diaphragm 66 and tubing 60 will be filled and the regulator tubes 56 will have been expanded to a point such that the pressures in the three regulator tubes 56 and the container 52 will be approximately equal. In the embodiment illustrated, assuming the container 52 to have been at an initial pressure of approximately 65 psi, the regulator tubes 56 and the container 52 of the pressurized system will each be at a pressure of approximately 12-14 psi.

As soon as the administration port 92 of the medicament bag 28 is pierced, the infusion set is filled with pressurized fluid up to the position of clamp 36. The air filter 32 serves the known purpose.

To start the infusion process, the infusion slide clamp 36 is released whereupon the expanded regulator tubes 56 are permitted to start to collapse due to the inherent resiliency thereof with the pressure being evenly exerted on the medicament bag 28 through the inflatable diaphragm 66 throughout the entire infusion process and until the medicament bag 28 has been substantially emptied.

The following formula explains how expansion of the regulator tubes controls the infusion pressure.

$$P_c V_c \text{ (a constant)} = P_i[x_i V_c + (4 - x_i) V_t + V_{Bag} + V_D]$$
$$= P_f[x_f V_c + (4 - x_f) V_t + V_D]$$

Figure 8:
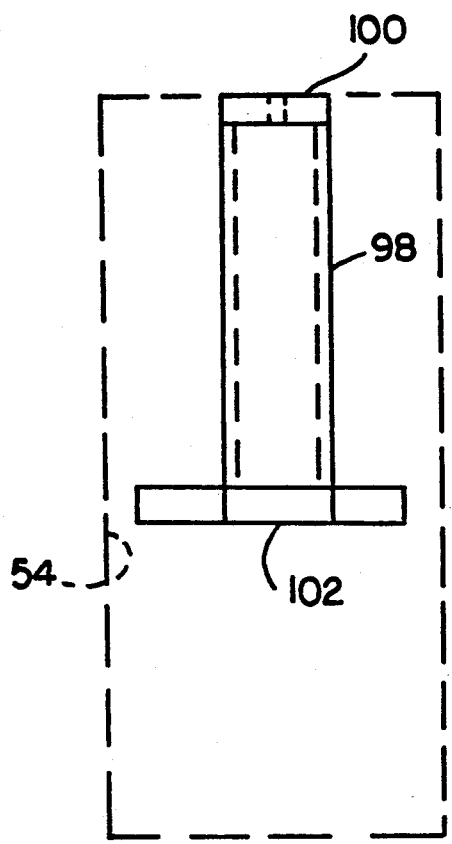
FIGS. 8 and 9 are top plan views of still another form of expandable regulator tube usable in the pressure system of FIG. 5 and showing same, respectively, before and after its expansion, the receiving cavity being shown in broken line for reference purposes.
Figure 9:
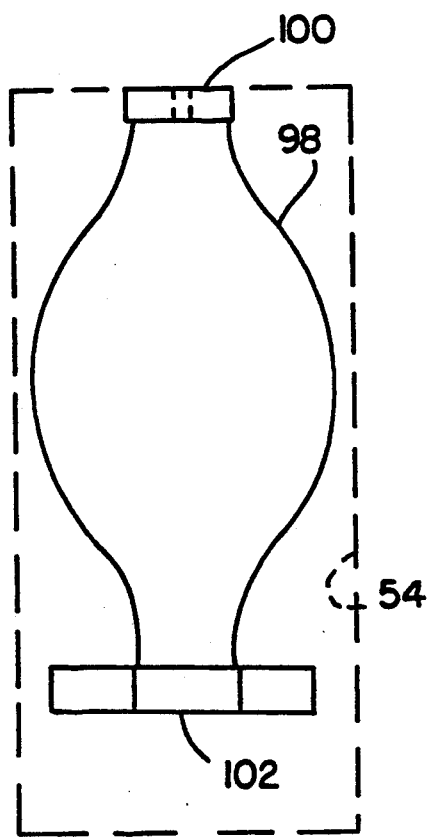
Figure 10:
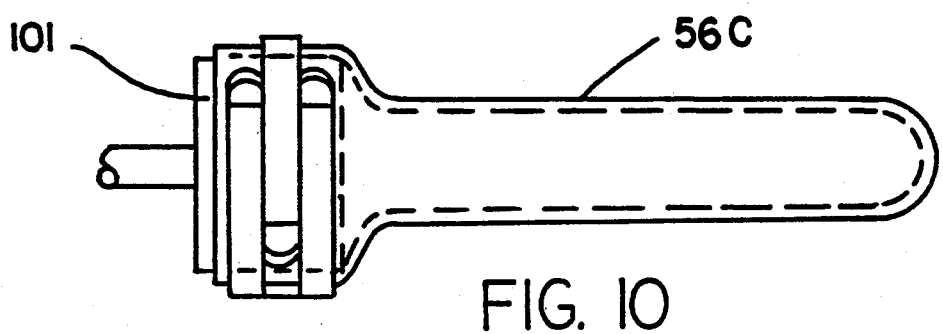
FIG. 10 is a side elevation view of the preferred form of regulator tube having a pre-stretched neck which is usable in the pressure system of FIG. 5.

Wherein:
- $p_c$ = Pressure of cannister (approx. 65 psi)
- $V_c$ = Volume of cannister
- $P_i$ = Initial pressure of system
- $P_f$ = Final pressure of system
- $V_t$ = Volume of each regulator tube
- $V_{Bag}$ = Volume of medicament bag
- $V_D$ = Volume of diaphragm
- $X_i$ = Number of regulator tubes initially inflated
- $X_f$ = Number of regulator tubes inflated at end of infusion Preferably initial $P_i = P_f$ As previously noted herein, the regulator tubes 56 may be of several different configurations and/or materials. The regulator tubes 56 shown in FIG. 5 may be described as pre-stretched tubes whereas FIG. 6 shows a tube 56a having a taper and FIG. 7 shows a tube 56b having a preformed annular outward bulge. It is understood that tapered tubes 56a may either have only a portion tapered or may be tapered throughout the entire length thereof. Likewise, annularly bulged tubes 56b may have one or more annularly bulged areas. FIGS. 8 and 9 illustrate another tube configuration wherein a length of tubing 98 open at both ends is provided at one end with a bored disc 100 clamped thereto for connection to one of the T-connectors 62 and with a larger non bored disc 102 clamped to the opposite end thereof. This embodiment is shown prior to pressurization in FIG. 8 and after pressurization in FIG. 9 whereby it will be noted that it has not only bulged but also lengthened in its cavity 54. A tube 56c having a pre-stretched neck is shown in FIG. 10. The fitment disc 101 stretches the proximal end of the tube so as to approach the yield pressure of the tube material. This insures the tube will expand from the fitment end. Suitable materials for use in fabricating such regulator tubes would include latex rubber with or without additives such as heat sensitive compounds by coagulating dip process.

The unique flow (or pressure) indicator 34 is characterized, as is best illustrated in FIG. 12, by a T-fitting 104, a pin holder 106, a pin 108, a spring 110 and a rubber diaphragm 112. When fluid is in the infusion set the diaphragm 112 is fully inflated and the pin 108 is disposed outwardly of its holder 106, as shown in broken lines, to indicate to the patient that he or she is still being infused.

After each treatment, single use items such as the infusion set 22, the medicament bag 28, and the pressurized gas container 52 can be disposed of. After a specified number of infusion treatments, or after one day, the entire ambulatory infusion device is discarded.

While there has been shown and described several possible embodiments of the invention, it will be obvious to those skilled in the art that changes and modifications may be made without departing from the invention, and it is intended by the appended claims to cover all such changes and modifications as fall within the true spirit and scope of this invention.

We claim:

1. An ambulatory infusion device comprising a flexible, filled medicament bag and a housing having an outlet port and first cavity means including an open cavity adapted to receive a pressurized gas container and a plurality of tube cavities, second cavity means including a cavity in said housing adjacent said outlet port and adapted to receive the flexible filled medicament bag having an administration port which extends from said housing through said outlet port for connection to a patient's infusion set, a flexible inflatable diaphragm underlying said medicament bag, a series of expandable regulator tubes disposed in tube cavities provided in said housing, said tube cavities being of a size permitting expansion of said tubes, passage means interconnecting said pressurized container cavity, said regulator tubes and said diaphragm whereby same are pressurized upon release of pressurized gas from a pressurized container disposed in said open cavity with said regulator tubes being expanded whereupon a substantially even pressure is applied by said diaphragm against said medicament bag to infuse the medicament into a patient at a steady rate during the entire infusion process and until said medicament bag is substantially emptied, the even pressure resulting from deflation of said regulator tubes.

2. The ambulatory infusion device of claim 1 wherein three regulator tubes are provided.

3. The ambulatory infusion device of claim 2 wherein each of said regulator tubes is provided with a slight taper from an open end to a closed end.

4. The ambulatory infusion device of claim 3 wherein each of said tapered tubes is provided with annular outwardly disposed bulge means disposed intermediate said open and closed ends thereof.

5. The ambulatory infusion device of claim 2 wherein each of said regulator tubes comprises a length of straight resilient tubing open at both ends with a bored fitting clamped onto one end for communication with said passage means and with a closed end fitting clamped onto the opposite end thereof, the non-pressurized length of said tubing being no greater than two-thirds of the length of the cavity in which it is disposed.

6. The ambulatory infusion device of claim 1 wherein the pressurized container is initially charged to approximately 65 psi and wherein each of said regulator tubes, after release of the gas from said pressurized cannister, is initially expanded within its cavity and charged to less than 15 psi, which charge becomes the pressure charge of the system which is maintained substantially constant during the entire infusion process with the system charge being continuously applied to said flexible medicament bag through the application of said system pressure thereupon through said inflatable diaphragm as a result of gradual deflation of said expanded regulator tubes.

7. An ambulatory infusion device comprising a three-part, sandwich-like housing characterized by a pair of upper and lower generally rectangular housing members and a third generally rectangular middle housing member sandwiched therebetween, means for maintaining said housing members in assembled relationship, first mating cavity means provided between said upper and middle housing members and second mating cavity means provided between said lower and middle members, said first cavity means defining cavities for a presurized gas container, for a series of expandable regulator tubes, for a diaphragm connector, and for tubing interconnecting a pressurized gas container, a series of expandable regulator tubes, and a diaphragm connector disposed in said first cavity means, said second cavity means defining a cavity for a flexible medicament bag having an administration port and an inflatable, substantially non-stretchable diaphragm adapted to underlie said medicament bag and to be connected to said pressure diaphragm connector, opening of said pressurized container filling said expandable regulator tubes to the extent permitted by the expandability of said tubes and inflating said diaphragm against said flexible bag through said diaphragm connector whereby the medicament in said flexible bag is infused through said administration port and a tube set into a patient at a controlled rate.

8. The ambulatory infusion device of claim 7 wherein three cavities are provided for three regulator tubes.

9. The ambulatory infusion device of claim 8 wherein the pressurized container is initially charged to approximately 65 psi and wherein each of said regulator tubes, after activation of said pressurized cannister, is initially expanded within its cavity and charged to approximately 15 psi, which 15 psi charge becomes the pressure charge of the system which is maintained substantially constant during the entire infusion process with the system charge being continuously applied to said flexible medicament bag through the application of said system pressure thereupon through said inflatable diaphragm as a result of gradual deflation of said expanded regulator tubes.

10. The ambulatory infusion device of claim 7 wherein a pair of ring like members are fitted over opposite ends of said three part housing to maintain said three part, sandwich like housing in assembled relationship.

11. An ambulatory infusion device comprising a three part, sandwich like housing characterized by a pair of upper and lower generally rectangular housing members and a third generally rectangular middle housing member sandwiched therebetween, a pair of slip-ring members fitted over opposite ends of said housing for maintaining said housing members in assembled relationship, first mating cavity means provided between said lower and middle housing members and second mating cavity means provided between said upper and middle housing members, said first cavity means defining cavities for a pressurized gas container, for a series of expandable regulator tubes, for a pressure diaphragm connector, and for tubing interconnecting a pressurized gas container, a series of expandable regulator tubes, and a pressure diaphragm connector disposed in said first cavity means, said second cavity means defining cavities for a bag clamp, for a flexible medicament bag having an administration port and an additive container associated therewith, and for a substantially non-stretchable, inflatable pressure diaphragm adapted to underlie a major portion of said medicament bag and to be connected to said pressure diaphragm connector, activation of said pressurized container filling and inflating said expandable regulator tubes to the extent permitted by the expandability of said tubes and inflating said pressure diaphragm against said flexible bag through said pressure diaphragm connector whereby the medicament in said flexible bag is infused through said administration port into a patient at a controlled rate.

12. The ambulatory infusion device of claim 11 wherein clamping means are provided for clamping off a part of said medicament bag.

13. The ambulatory infusion device of claim 11 having a pressure relief valve provided therein.

14. The ambulatory infusion device of claim 11 having a tube set associated therewith, which tube set has a pressure indicator provided therein.

* * * * *